(12) United States Patent
Raymond

(10) Patent No.: US 8,165,901 B2
(45) Date of Patent: Apr. 24, 2012

(54) METHOD AND SYSTEM FOR DEVELOPING OR TRACKING A PROGRAM FOR MEDICAL TREATMENT

(76) Inventor: Heather Raymond, New York, NY (US)

(*) Notice: Subject to any disclaimer, the term of this patent is extended or adjusted under 35 U.S.C. 154(b) by 323 days.

(21) Appl. No.: 12/148,916

(22) Filed: Apr. 23, 2008

(65) Prior Publication Data

US 2009/0023555 A1    Jan. 22, 2009

(51) Int. Cl.
*G06F 19/00* (2011.01)
(52) U.S. Cl. ......... 705/3; 705/2; 482/8; 482/9; 340/7.48
(58) Field of Classification Search .................. 705/2, 3; 482/8, 9; 340/7.48
See application file for complete search history.

(56) References Cited

U.S. PATENT DOCUMENTS

| | | | | |
|---|---|---|---|---|
| 6,159,131 A * | 12/2000 | Pfeffer | ............................... | 482/8 |
| 6,579,209 B1 * | 6/2003 | Valette et al. | ..................... | 482/8 |
| 6,827,670 B1 * | 12/2004 | Stark et al. | ......................... | 482/9 |
| 7,169,085 B1 * | 1/2007 | Killin et al. | ....................... | 482/8 |
| 2002/0033753 A1 * | 3/2002 | Imbo | ............................ | 340/7.48 |
| 2003/0171189 A1 * | 9/2003 | Kaufman | ...................... | 482/8 |
| 2007/0136093 A1 * | 6/2007 | Rankin et al. | ...................... | 705/2 |

OTHER PUBLICATIONS google patent search.*
google patetns search results, Mar. 9, 2011.*

* cited by examiner

*Primary Examiner* — Dilek B Cobanoglu
(74) *Attorney, Agent, or Firm* — Stroock & Stroock & Lavan LLP

(57) ABSTRACT

This invention relates generally to a system and method for providing to patients a medical treatment program, such as a program for physical therapy, and for tracking whether the patient has performed the program correctly. In one aspect, the system and method determines whether the patient has performed the program correctly by comparing feedback from the patient for various parameters associated with an exercise to anticipated values for those parameters. In another aspect, the invention assists medical treatment providers in selecting exercises and tutorials to include in the medical treatment program.

3 Claims, 12 Drawing Sheets

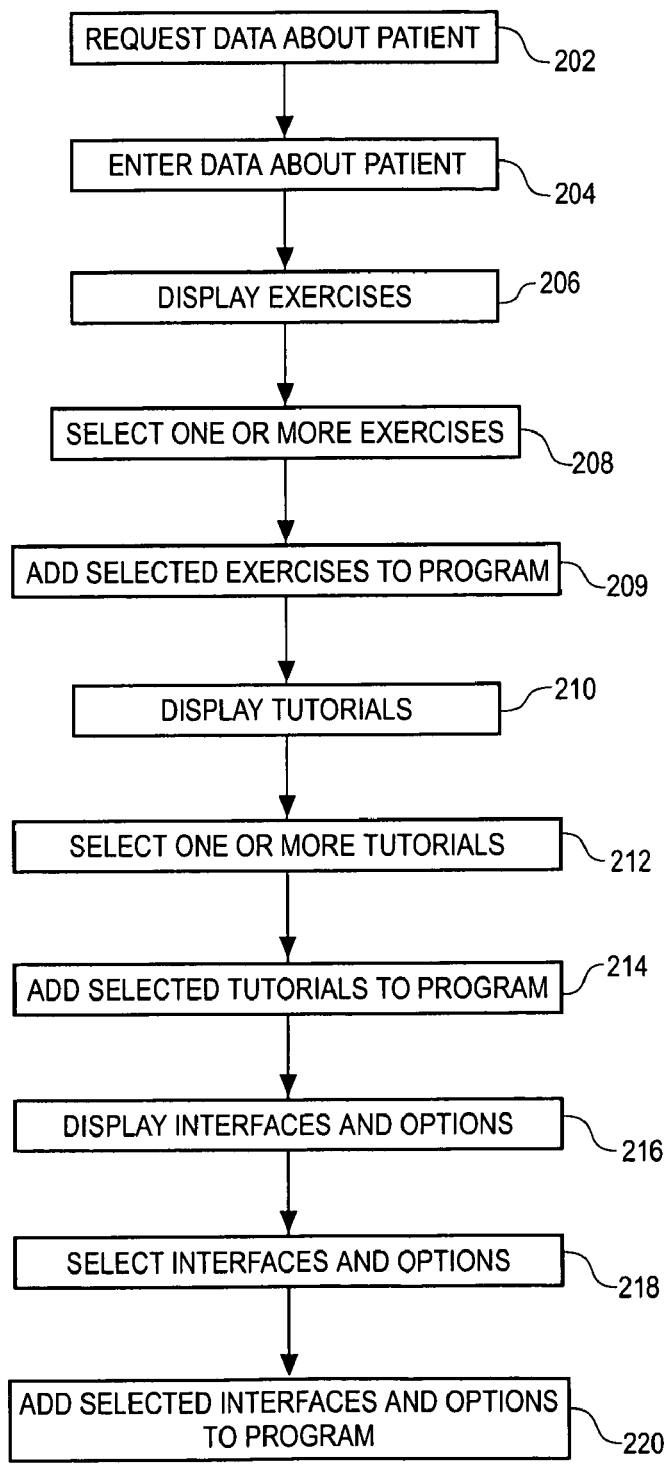

Fig. 4G

Heather A. Raymond

⑥ Give the Gift of Motion  1/3

① Get patient's profile
② Locate the problem
③ Exercise Customization 1
④ Exercise Customization 2
⑤ Related Tutorials
⑥ Give the gift of Motion
⑦ PT Profile RxOM PT Service Interface to Ipod/MP3 player?
brand [Apple] [Other device]
model [Ipod/Nano]
Interface to a palm? No ☐  Yes ☑
brand [Pilot]  number [917 444 5555]
model [605X]  carrier
Interface to cellphone? No ☐ Yes ☑
brand [Nokia]  number [917 444 5555]
model [6110]  carrier [Verizon]
Save [select]
  3DHab.com
  Burn CD
  Burn DVD
  Others

[Save]

Heather A. Raymond

⑥ Give the Gift of Motion  2/3

① Get patient's profile
② Locate the problem
③ Exercise Customization 1
④ Exercise Customization 2
⑤ Related Tutorials
⑥ Give the gift of Motion
⑦ PT Profile RxOM PT Service Do you want to enable graphics? [select...]
  motivational
  instructional
  educational
  optional feedback
☑

Language [English]  🔊 Audio [English]
  Spanish    Spanish
  French     French
  Italian    Italian
  Russian    Russian Closed captions [English]
  Spanish
  French
  Italian
Text Message Alert [select...]  Russian
  1.Once
  2.After Missed
  3.With each frequency
  4.Random
  5.To PT if patient missed
  6.To PT if patient logged on Time Saver Treatment
No ☑  Yes ☐  [Preset]

Heather A. Raymond

① Get patient's profile
② Locate the problem
③ Exercise Customization 1
④ Exercise Customization 2
⑤ Related Tutorials
⑥ Give the gift of Motion
⑦ PT Profile ❼ Grow your business
Save your profile Dr. Smith Click on this link to save your info and additional services your office provides that may aid your patients in your pursuit of health Click here if you would like RxOM to notify you when a patient clicks the link and needs more information ( Edit )  ( Save ) ⌒416

Doctor Profile and Related Information about additional services offered by the office [ grow your business with RxOM ]

RxOM PT Service

For more information please visit www.RxOM.com

METHOD AND SYSTEM FOR DEVELOPING OR TRACKING A PROGRAM FOR MEDICAL TREATMENT

FIELD OF THE INVENTION

This invention relates generally to a method and system for providing and tracking a program for medical treatment. More particularly, the present invention facilitates the development of a treatment program, the retrieval of the program by the patient, the tracking of the patient's use of the program, the entry of feedback about the program by the patient, and the processing of that feedback.

BACKGROUND

Physical therapy is often prescribed for patients as a program for rehabilitation following injury, sickness, a surgical operation, etc. But physical therapy programs often require a patient to perform a substantial amount of unsupervised exercise at home. As a result, patients sometimes do not perform the exercises properly or do not perform them at all.

Various approaches have been made to improve home therapy programs. These approaches include providing illustrations and text about the exercises to the patient. Other attempts include providing videos of models performing the exercise accompanied by stock narrations of the exercise. The illustrations, videos and text can be provided to the patient by email.

These approaches, however, have shortcomings. Patients often do not find the correct form of the exercise because the illustrations and video are not customized for each patient. Moreover, these approaches do not track whether the patient performed the prescribed exercises and performed them correctly. Accordingly, patients often do not benefit from the home exercise programs. Consequently, health insurance companies may expend money on physical therapy that is not effective.

In addition, physical therapy patients may also benefit by properly using other health care products or services in conjunction with their physical therapy programs. For example, a patient may recover more rapidly from a back injury if he or she sleeps in the proper position in the proper type of bed, uses a wheelchair properly, etc.

Accordingly, there exists a need for a method and system to facilitate the development of physical therapy programs that are tailored to a patient's condition. There also exists a need for a method and system that tracks whether the patient is performing the prescribed exercises at home and that provides instruction to the patient as to how to perform the exercise properly. Finally, there exists a need for a method and system to identify other health care products or services that may be helpful to a physical therapy patient.

SUMMARY OF THE INVENTION

The invention provides a system and method to facilitate the development of physical therapy programs that are tailored to a patient's condition. The invention also provides a system and method that tracks whether the patient is performing the prescribed exercises at home and assists the patient in performing the exercises properly. The invention also provides a system and method to identify other health care products or services that may be helpful to a physical therapy patient.

In particular, it is an aspect of the present invention to provide a medical treatment program comprising: a first module executing on one or more servers for receiving data about the patient; a first browser executing on a first computer and communicating with said first module, for displaying one or more exercises relating to said patient and for selecting at least one of said exercises for inclusion in a program; a second module executing on said one or more servers for displaying at least one of said exercises in said program to the patient and for collecting feedback on said at least one exercise from the patient, and a database for storing said program and said feedback.

It is a further aspect of the present invention to present a method for providing a medical treatment program comprising the steps of: receiving data on a patient, said data comprising one or more of the following: an identification of a body part of the patient that has an ailment, and a description of the ailment; displaying one or more exercises relating to the ailment; selecting at least one of said exercises for inclusion into the program; displaying one or more tutorials on one or more subjects relating to said patient data; and selecting at least one of said tutorials for the program.

BRIEF DESCRIPTION OF THE DRAWINGS

These and other aspects and features of the invention will be more clearly understood from the following detailed description along with the accompanying figures, wherein:

FIG. 2 is a dataflow diagram illustrating the development of a physical therapy program.

FIGS. 4a, 4b, 4c, 4d, 4e, 4f, 4g, 4h, and 4i display sample panels that are completed by a physical therapist to enter data that will be used in the development of a physical therapy program.

Figures 5E, 5F:
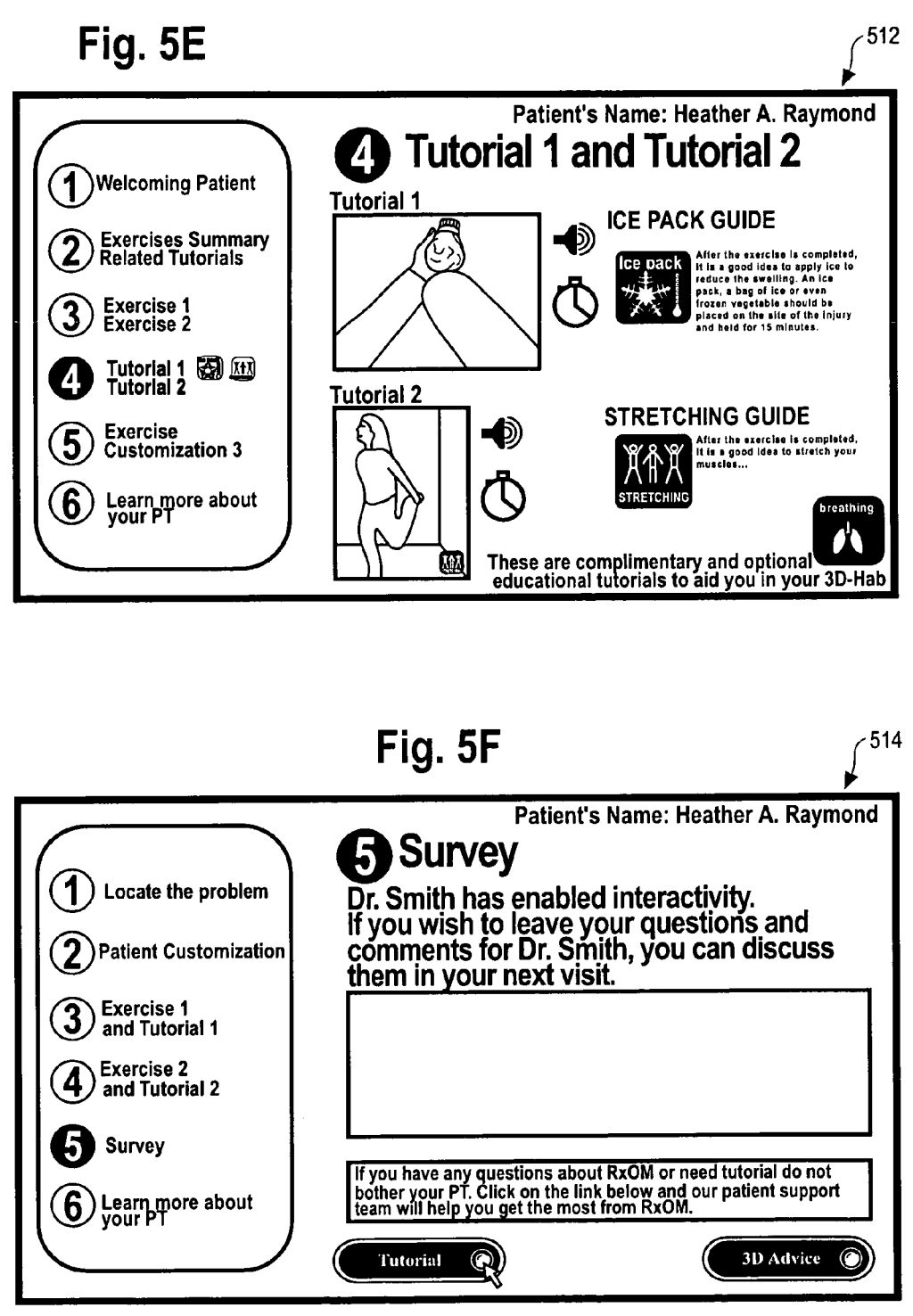

FIGS. 5a, 5b, 5c, 5d, 5e, and 5f display sample panels that are used by the patient to learn how to perform the prescribed exercises at home or to provide feedback on the performance of those exercises.

DETAILED DESCRIPTION OF THE PREFERRED EMBODIMENT

This invention relates generally to a method and system for developing or tracking a program for medical treatment. More particularly, the present invention facilitates the development of a treatment program, the retrieval of the program by the patient, the entry of feedback about the program by the patient, and the processing of that feedback.

While the present invention will be explained within the context of a physical therapy program, the present invention can be applied to other treatment programs in which there is a need to track whether the patient is following the program and to assist the patient in correctly doing so. Such treatment programs include developing or tracking programs for taking medicine, sleeping, eating, occupational therapy, speech pathology, care after surgery, infant care, treating infections including ear infections, etc.

Figure 1:
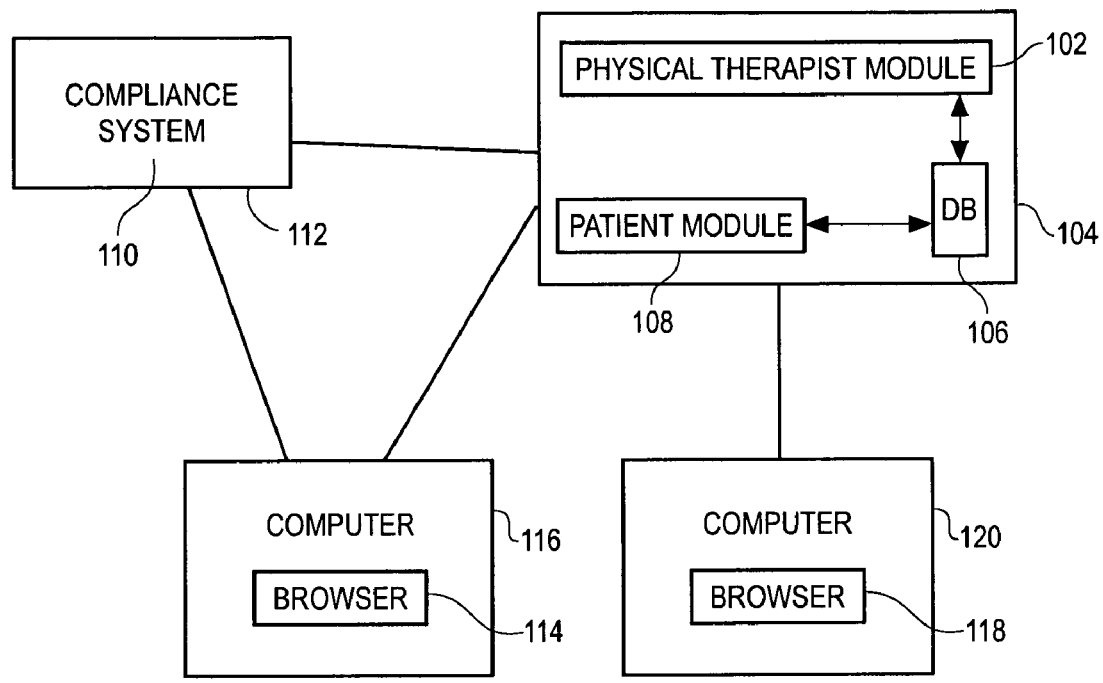
FIG. 1 is a block diagram showing the major operational elements of the invention.

FIG. 1 is a block diagram showing the major operational elements of the invention. The invention may include a physical therapist module 102 executing on a server 104. The physical therapist module 102 collects data from a physical therapist regarding a treatment program for a patient, processes that data, and stores it in a database 106.

The invention may further include a patient module 108 executing on a server 104. The patient module 108 may display video and text instructions to the patient regarding the patient's treatment program. It may also collect data from the patient tracking the patients performance of the program, process the data specified by the patient, and store the data in a database 106.

In one embodiment, Hypertext Markup Language (HTML) pages are used to input data from a physical therapist or a patient. The physical therapist module may be a script executing on the server 104. An exemplary scripting tool is Cold Fusion, which is a tool for creating World Wide Web applications by combining HTML files with Cold Fusion Markup Language (CFML) tags. Exemplary databases 106 include Microsoft SQL Server, Microsoft Access, Microsoft FoxPro, Oracle, Borland Paradox and Microsoft Excel.

The invention may further include a compliance module 110. The compliance module 110 tracks whether the patient is following the prescribed home exercise program by analyzing the data gathered from the patient by the patient module 108. The compliance module 110 may execute on another server 112. Alternatively, the compliance module 110 may execute on the same server 104 as the physical therapist module 102 or the patient module 108. The compliance module 110 may communicate with the patient module 108 and/or retrieve data from the database 106.

The invention may also include a browser 114 executing on a computer 116 for the physical therapist. The browser 114 may communicate with the physical therapy module 102. In particular, the physical therapy module 102 may transmit web pages to the browser 114 executing on the physical therapist's computer 116. The browser 114 may transmit data, including data regarding the physical therapy program entered by the physical therapist on the web pages, to the physical therapy module 102.

The browser 114 may also communicate with the compliance module 110 and the compliance system 110 may communicate with the patient module 108. In particular, the patient module 108 may transmit data, including data indicating whether the patient has complied with his or her home exercise program, to the compliance module 110. And the compliance module 110 may communicate this data to the browser 114 executing on the physical therapist computer 116.

The invention may also include a browser 118 executing on a computer 120 for the patient. The browser 118 may communicate with the patient module 108. In particular, the patient module 108 may transmit web pages to the browser 118. The browser 118 may, in turn, transmit data, including data indicating whether the patient has complied with his or her exercise program, to the patient module 108.

The database 106 may contain information regarding physical therapy programs for one or more patients and information indicating whether the programs have been followed by the patient. The physical therapy module 102 and patient module 108 may communicate with the database 106.

FIG. 2 is a dataflow diagram illustrating the development of a physical therapy program 200. In step 202, data regarding the condition of the patient is requested. This data may include an identification of the portion of the body that is injured (i.e., knee), a description of the ailment (i.e., muscular imbalance), etc. In step 204, data regarding the condition of the patient is entered. In step 206, exercises that may be helpful for the patient's condition are displayed. In step 208, one or more of the displayed exercises are selected. In step 209, the selected exercises are added to the patient's physical therapy program. In step 210, tutorials on subjects that may also be helpful for the patient's condition are displayed. Exemplary subjects including ice application, stretching, massage, heat application, compression, safety, education, brace usage, ultrasound usage, relaxation exercise, proper sleep suggestions, ergonomics, dietary suggestions, functional movements, teeth brushing, getting out of bed, computer ergonomics, etc. In step 212, one or more of the tutorials are selected. In step 214, the selected tutorials are added to the patient's physical therapy program. In step 216, various types of interfaces and options about the interfaces are displayed. The interfaces may include an Ipod/MP3 player, a Palm handheld computer, a cell phone, etc. Options about the interfaces may include the brand, the model, etc. In step 218, an interface, along with one or more options about the interface are selected. In step 220, the selected interface and options are added to the patient's physical therapy program.

Figure 3A:
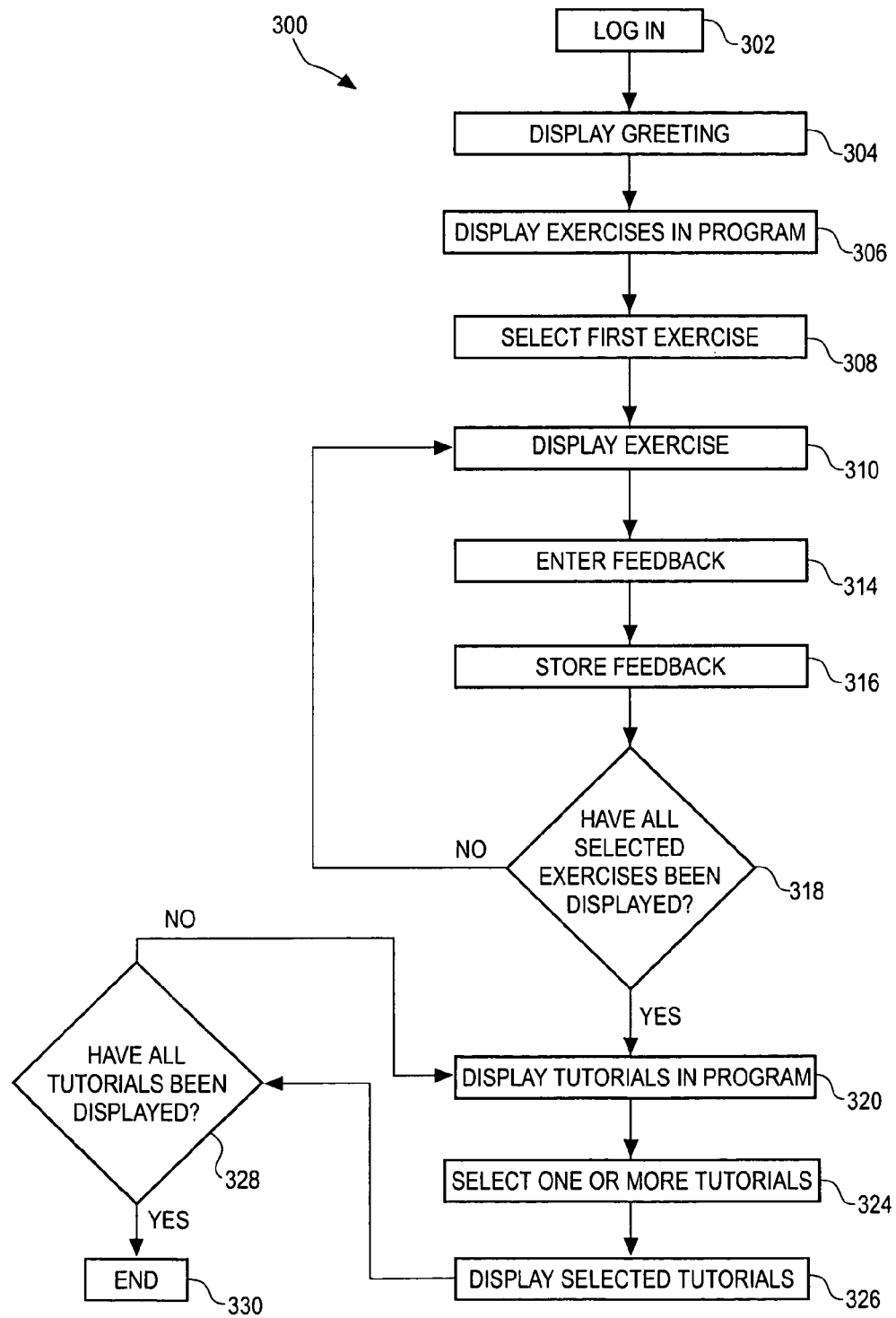
FIG. 3a is a dataflow diagram illustrating the display of the physical therapy program and the entry processing of feedback from a patient.

FIG. 3a is a dataflow diagram 300 illustrating the display of the physical therapy program to the patient and the entry and processing of feedback from a patient. In step 302, a patient logs into the system. In step 304, a greeting is displayed to the patient. In step 306, a list of exercises from the patient's physical therapy program are displayed. In step 308, the first exercise in the program is selected. In step 310, the selected exercise is displayed. The display may include audio, video and/or textual data. Also, information about the date and time the patient started the exercise is sent to the compliance system 110. In step 314, feedback is entered by the patient. Feedback may include a rating of the difficulty of the exercise by the patient and/or a rating of the pain experienced by the patient in performing the exercise. In step 316, the feedback is stored. Also, information regarding the feedback and the date and time it was entered by the patient is sent to compliance system 110.

In step 318, a check is performed to determine whether all the exercises have been displayed. If all of the exercises have not been displayed, then control goes to step 310, in which the next exercise in the program is displayed. If all of the exercises have been displayed, then control proceeds to step 320.

In step 320, a list of tutorials from the patient's physical therapy program are displayed. In step 324, one of the tutorials may be selected. In step 326, the selected tutorials is displayed. The display may include audio, video and/or textual data.

In step 328, a check is performed to determine whether the patient would like to display another tutorial. If so, then control goes to step 320. If all of the tutorials that the patient would like to see have been displayed, then control proceeds to step 330.

Figure 3B:
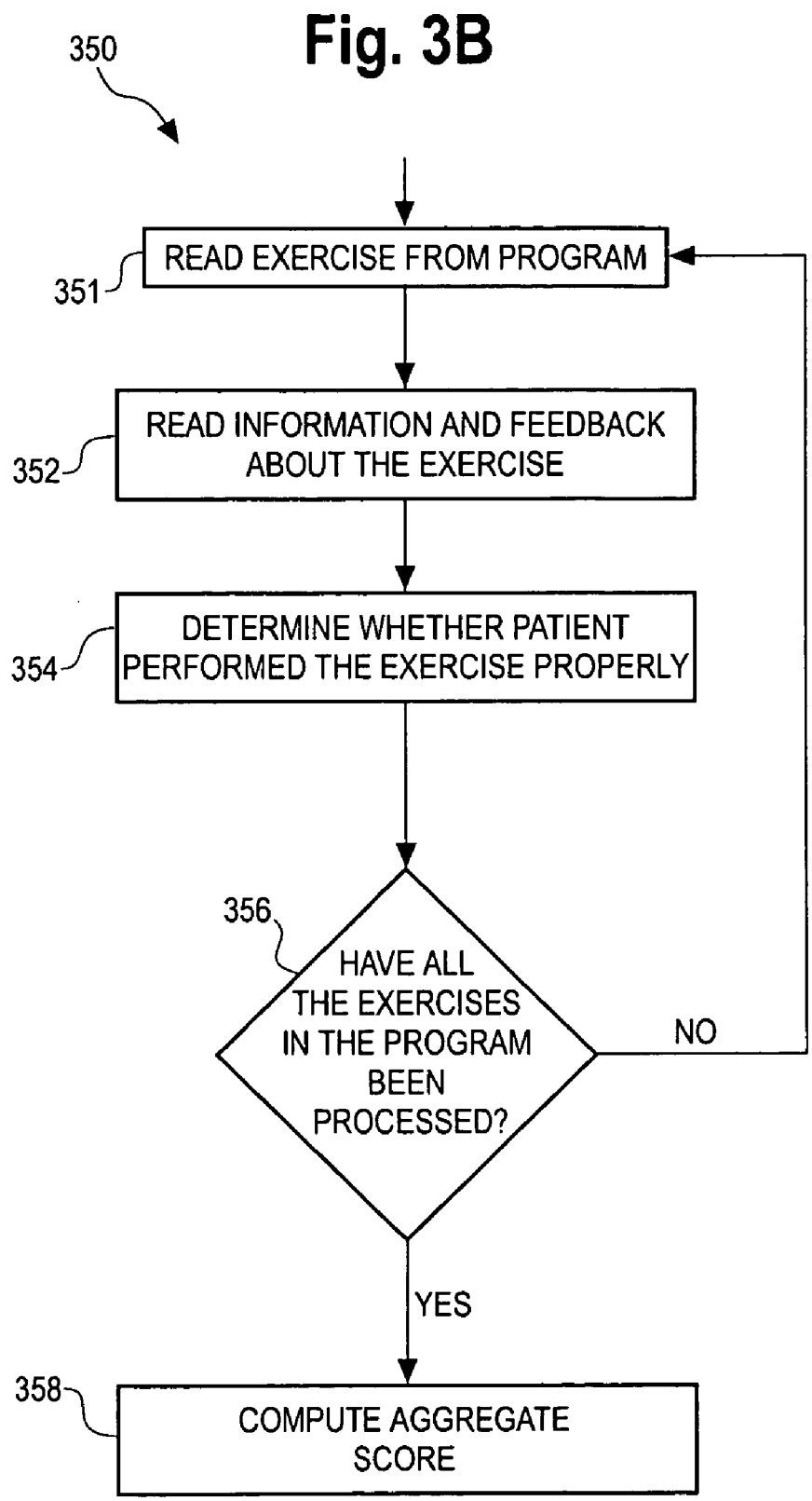
FIG. 3b is a dataflow diagram illustrating a determination of the likelihood that a patient complied with the physical therapy program based on information about the program and the feedback entered by the patient.
Figure 4A:
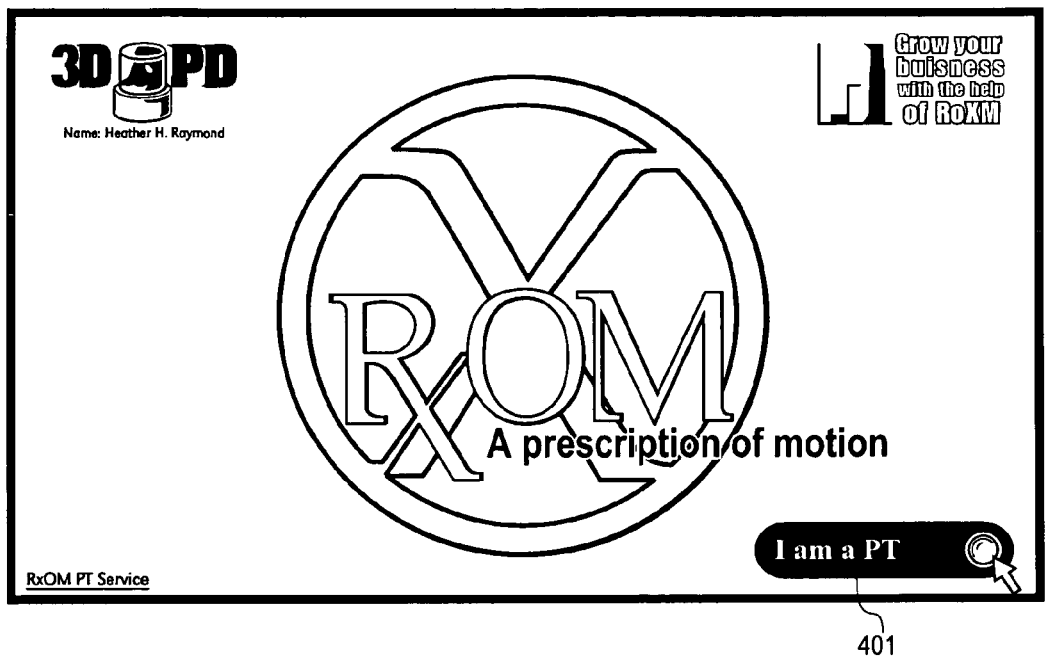
Figure 4B:
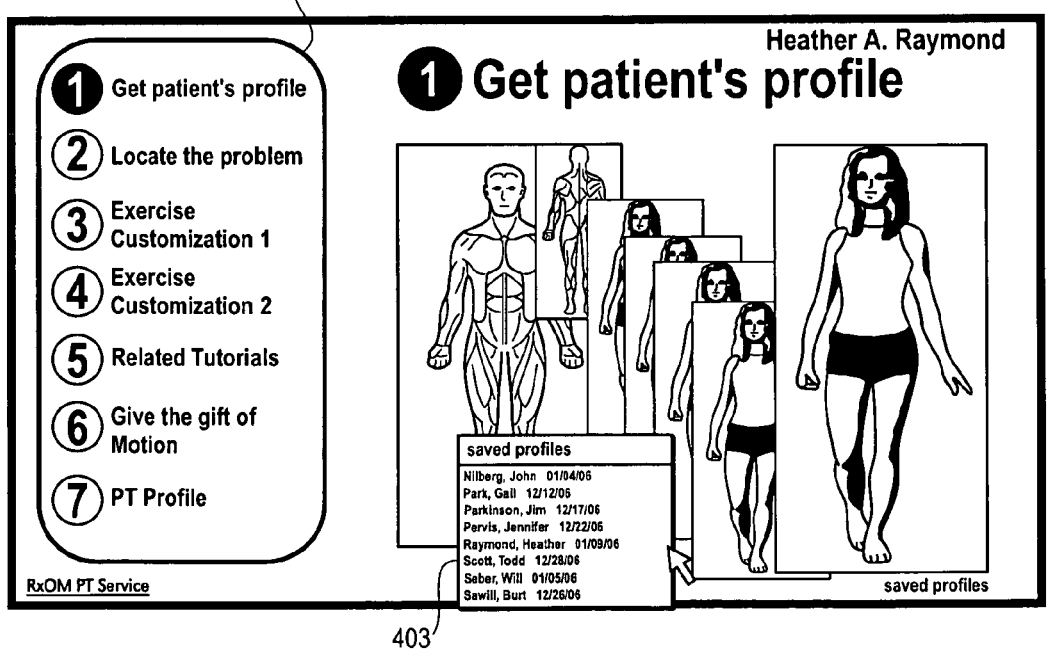
Figure 4C:
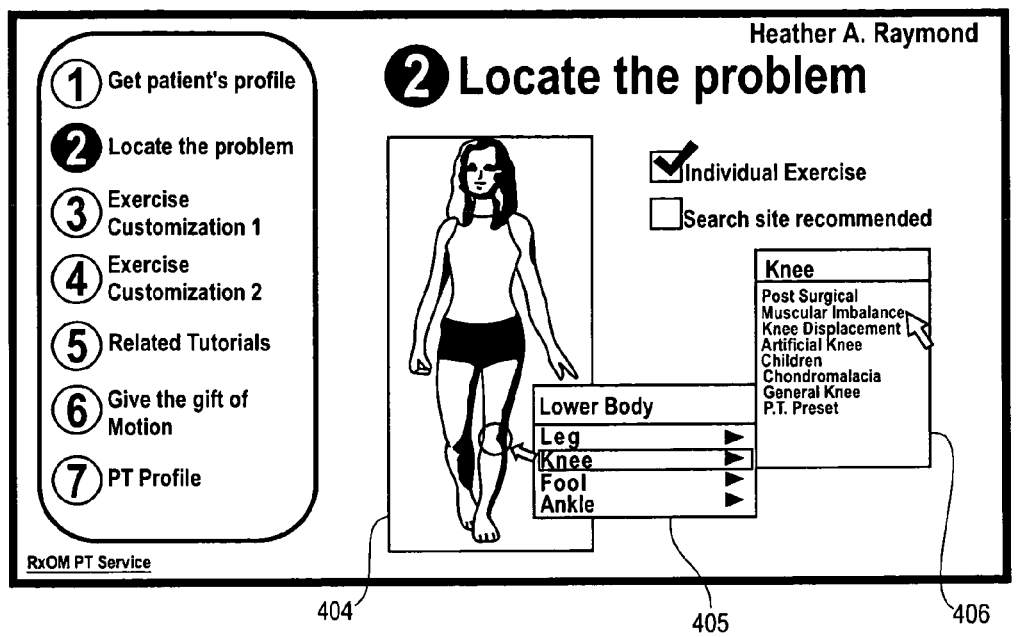
Figure 4D:
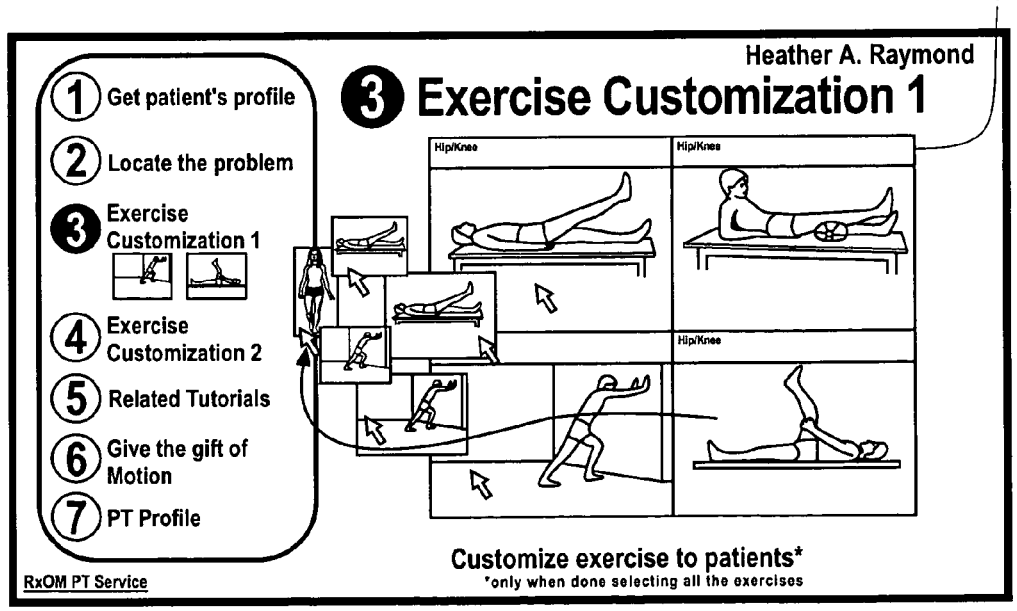
Figures 4E, 4F:
Figure 5A:
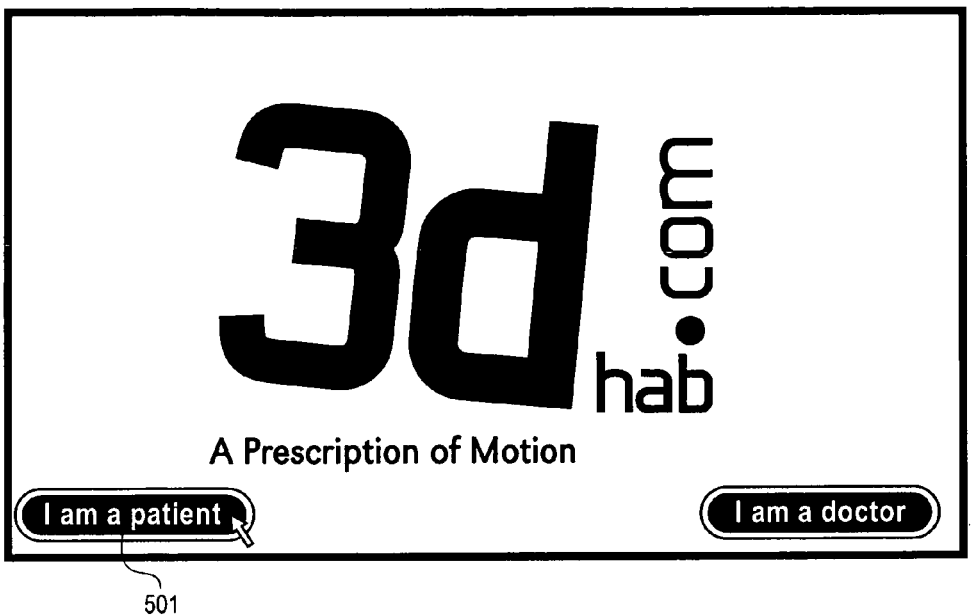
Figure 5B:
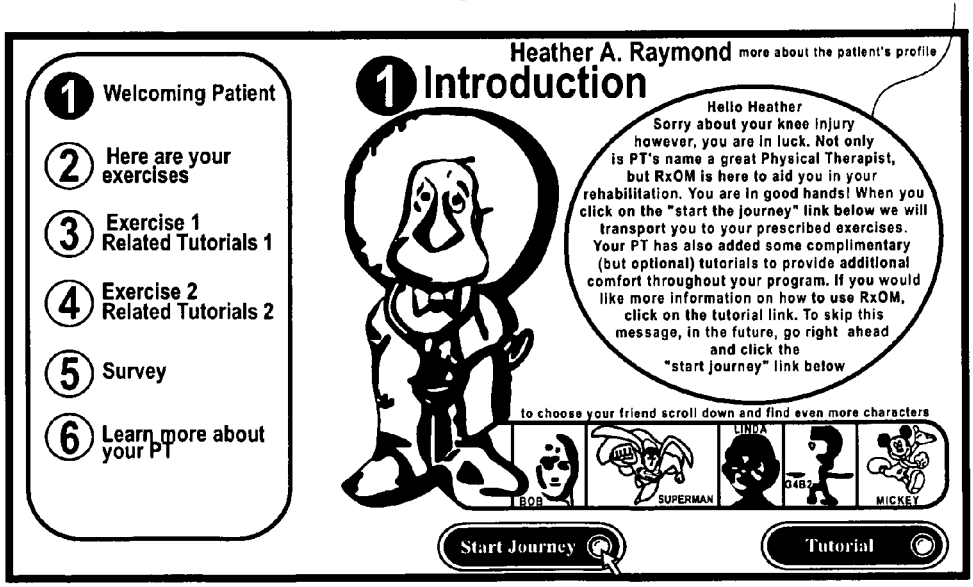
Figure 5C:
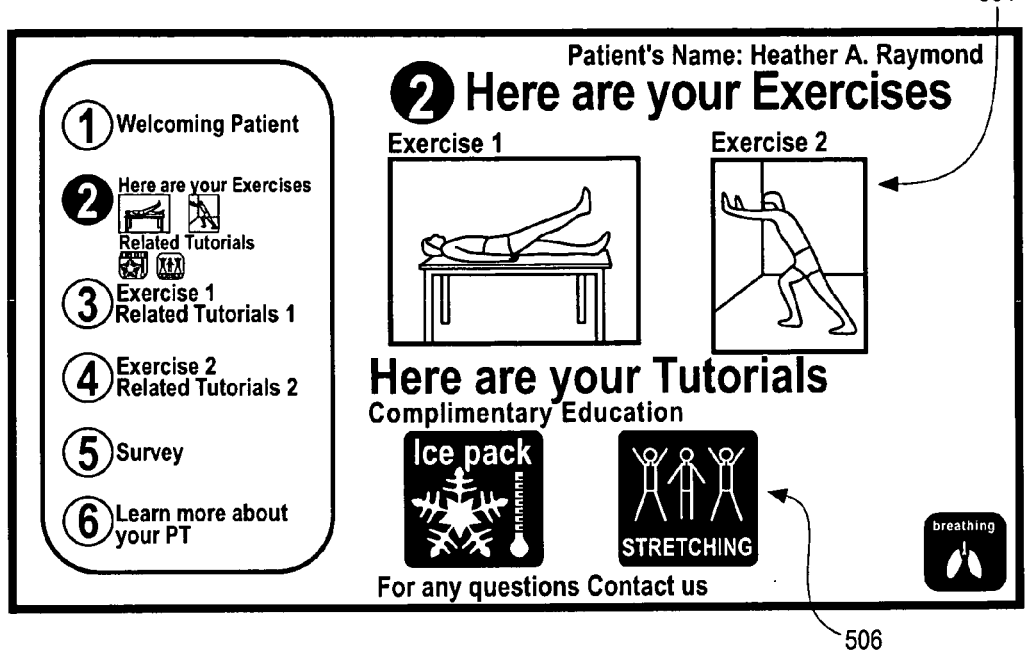
Figure 5D:
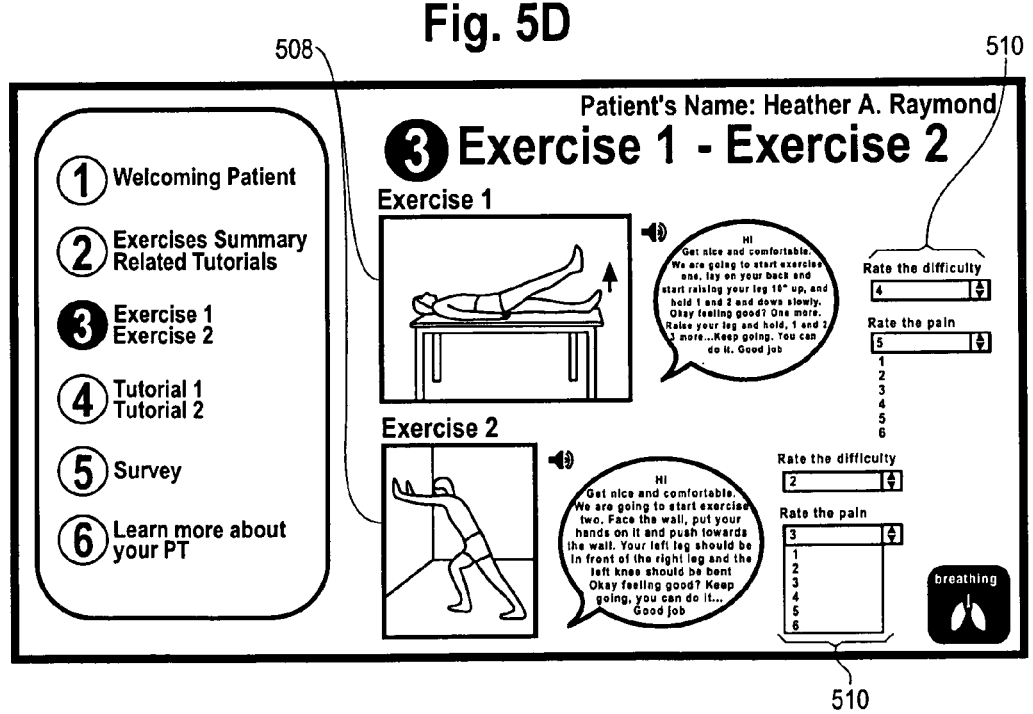

FIG. 3b is a dataflow diagram 350 illustrating a determination by the compliance system of the likelihood that a patient complied with the physical therapy program based on information about the program and the feedback entered by the patient. In step 351, an exercise from the patient's physical therapy program is read. In step 352, information and feedback associated with a particular exercise is read. The information and feedback may include the time the exercise was displayed to the patient, the time the patient entered the feedback, the level of difficulty and/or pain entered by the patient, etc. In step 354, a determination is made of the likelihood that the patient performed the exercise properly. For example, if an exercise is estimated to take three minutes and the difference between the time that the exercise was displayed and the time that the patient entered feedback is thirty seconds, than the likelihood that the exercise was performed properly is determined to be low. In this manner, a score measuring how well the patient performed an exercise within the patient's physical therapy program is determined.

In step 356, a check is performed to determine whether all the exercises in the patient's physical therapy program have been processed. If all of the exercises have not been processed, then control returns to step 351. If all of the exercises have been processed, then control proceeds to step 358. In step 358, an aggregate score is computed as to how well the patient performed his or her physical therapy program. The aggregate score may be computed by combining the individual scores for one or more of the individual exercises within the program. If the compliance system determines that the patient has not been performing his or her exercises or has not been doing them properly, the compliance system may send an alert to the physical therapist. The alert may be in the form of an email, text message, phone call, or any other suitable form.

FIGS. 4a, 4b, 4c, 4d, 4e, 4f, 4g, 4h, and 4i display sample web pages that are completed by a physical therapist in entering data that will be used in the development of a physical therapy program for a particular patient. The web pages may include one or more of the following fields:

Physical therapist indicator 401: This field may include a button that is selected by a physical therapist to launch the web pages for developing a physical therapy program for a patient.

Menu 402: This field may include a menu for selecting one of several options.

Saved Profile 403: This field may contain a list of profiles that had been previously saved for one or more patients. The field may also include the date that the profile was created. It may also include the date that the profile was last revised.

Body Image 404: This field may contain an image of a body.

Body Part Menu 405: This field may contain a menu listing the body parts.

Body Part Ailment Menu 406: This field may contain a list of ailments that may be associated with a body part. The Body Part Ailment Menu 406 for a particular body part may be displayed by selecting the body part from the body part menu 405.

Exercise Customization I 407: This field may include sketches of exercises that may be helpful for a particular ailment. The field may also include a scroll down menu to display sketches of additional exercises, should the number of available exercises exceed the number that can fit on a web page. Exercises may be selected for a patient by dragging the image of that exercise to an icon representing the patient.

Exercise Customization II 408: This field may include more detailed information about the exercises in a patient's program including the number of sets, the number of repetitions per set, the frequency (number of times per day that the sets should be performed), the start date for the exercise, the end date for the exercise, miscellaneous notes, etc.

Exercise Video 409: This field may include videos of exercises. In one embodiment, the body type of the person doing the exercise in the video is selected to be similar to that of the patient. In another embodiment, the face of the patient is imposed on the person doing the exercise in the video. A video of the exercise is then generated that follows the detailed exercise information entered by the physical therapist.

Related Tutorials 410: This field may include a listing of tutorials on other topics that may be helpful to a patient including ice, stretching, massage, heat, compression, safety education, brace, ultrasound, relaxation, proper sleep suggestions, ergonomics, dietary suggestions, functional movements, brushing teeth, getting out of bed, computer ergonomics, etc. In one embodiment, a topic is selected by clicking and dragging it to a "selected tutorials" icon. Providers of health care services and goods (i.e., wheelchairs) may provide tutorials for use in the invention.

Interface Selection 412: This field may include a menu of the possible interfaces that are available to the patient including an IPOD/MP3 player, a Palm handheld computer, a cellphone, etc. The menu may also include a listing of the available brand and models for each interface. This field also includes items for selecting the type of interface, brand, model, etc.

Interface Options 414: This field may include a menu of selections for graphics, language, text message alerts, etc. This field may also include an option called "Time Saver Treatment" that enables the physical therapist to save time by selecting a set of defaults rather than to make each selection separately.

Save Profile 416: This field may contain a link to save a profile containing information about, for example, the physical therapist and services offered by the physical therapist and a link to edit the profile.

FIGS. 5a, 5b, 5c, 5d, 5e, and 5f display sample web pages that are used by the patient in performing the prescribed exercises at home and/or to provide feedback on the performance of those exercises. The web pages may include one or more of the following fields:

Patient indicator 501: This field may include a button that is selected by a patient to launch the web pages for performing the prescribed exercises and/or to provide feedback on the exercises.

Introduction 502: This field may include a greeting to the patient. The field may be displayed after the patient logs into the system.

Exercise List 504: This field may include one of more exercises in the patient's physical therapy program.

Tutorial List 506: This field may include one or more tutorials on subjects such as ice application, stretching, massage, heat application, compression, safety education, brace, ultrasound, relaxation, proper sleep suggestions, ergonomics, dietary suggestions, functional movements, brushing teeth, getting out of bed, computer ergonomics, etc.

Play Exercise 508: This field may include the playing of a video, audio, and/or textual presentation of the exercise.

Exercise Feedback 510: This field may include one or more questions to the patient about the exercise including how the patient would rate the difficulty and pain of the exercise.

Play Tutorial 512: This field may include the playing of a video, audio, and/or textual presentation of a tutorial.

Survey 514: This field may include an area for receiving textual feedback from the patient about the exercise.

The present invention may be used in various settings including Physical Therapy (PT), Occupational Therapy (OT), Speech pathology (SP), a Primary caregiver including a Medical Doctor (MD), a Chiropractor (DC), a Medical Athletic Trainer (AT), and other health professional (OHP), Insurance companies, Medicare/Medicaid, an Inpatient Facility such as a hospital, rehabilitation centers, assisted living and administrators who provide care, educational institutions, and "wellness in the workplace" programs (collectively referred to hereinafter as "Health/Medical Services Organizations").

In one aspect of the present invention, a patient or end user's care plan may be customized. Instructions for care may be left with the patient or end user, or to other parties who are providing care to the patient or end user. In the case, for example, of Physical Therapy, Occupational Therapy, and Speech Pathology, an interactive, take-home exercise program may be created. The take-home program—through patient participation—supports the therapeutic treatment plan and its therapeutic goals. With the present invention, the quality and efficiency of the therapeutic interaction is enhanced and opportunities for profit within the transaction are created. Also, opportunities for moral hazard/adverse selection and fraud are minimized.

In one embodiment, the present invention includes a monitoring, evaluation, and compliance feature. This feature may monitor the patient's compliance with the prescribed exercise, and may collect feedback from the patient by asking questions and receiving responses, and/or through self-reporting by the patient. In one embodiment, a compliance system records various events such as a patient login, patient reporting, patient's responses to questions, etc. Reports on the patient's compliance may be delivered to the Health/Medical Services Organizations. A patient may be reminded by email or telephone if he or she fails to comply with the program. In one embodiment, communication with a patient may be done through the Internet. In another embodiment, communication may be done through the telephone system.

In one embodiment, the present invention includes a tracking device/sensor tag that gathers data about the patient and communicates that data. For example, a tag may be worn on a muscle to determine whether a patient has performed an exercise over a full range of motion and to transmit that information to one or more Health/Medical Services Organizations. Information collected from a tag may be used to monitor compliance, track and evaluate progress toward therapy objectives and patient healing, correct misunderstandings by the patient, and help the patient achieve proper form.

In one embodiment, the present invention may include animated avatar characters using motion capture to collect the data and medical animation to render exercises. The animated avatar characters may be user-customizable. A health/medical service provider may add the sets/reps/frequency and special therapy notes for each exercise. The exercise may be played for a patient as if it was a customized workout video.

In one embodiment, the patient may create at intake an on-line image of himself or herself. The patient can customize the look, outfit, age, defining characteristics, etc. One or more of the Health/Medical Services Organizations may use this character to customize a patient's prescription.

An avatar may act as a tour guide and lead the patient through the application, introducing the patient to understand the health/medical services provider's instructions, and the body's reaction to the process.

Graphics, guidelines and motivational messages and feedback encourage proper form and patient participation. A health/medical services provider may take control over the patient form (even though the provider is not present), increasing the chances the patient will remember the special instructions that were discussed with the patient in the face-to-face setting.

Communications between the patient and a Health/Medical Services Organization, including patient feedback, may occur via communication methods selected by the patient or the Service Organization, thereby adding interactivity.

The present invention increases the likelihood and incentive for physical therapists to provide holistic care and to create a profit model that makes such detailed education cost effective. For example, a health/medical services provider can select tutorials for a patient from a database of video tutorials. The tutorials may guide the patient on a step-by-step basis through various tasks and activities. More generally, after a health/medical services provider has prescribed an exercise protocol, it may provide patient education for after care and on-going care. Such care may include: Patient education, rehabilitation products and services, patient comfort, health care initiatives etc., wellness topics, additional comfort suggestions, "how to's", appropriate medical information, third party tutorials, pre- and post-operative care, long term illness care, buddy support to assist a loved one in the recovery, etc. Patients can get that education in the comfort of their homes, in the delivery method of their choosing, and can repeatedly view it until they understand.

In another embodiment, a health/medical services provider can provide information relating to a patient's exact range of motion and exact desired range of motion. The on-line avatar will then perform the exercise in the range that is expected of the patient, aided by motion capture technology for the patient's specific protocol.

One embodiment of the present invention may be used for people with special disabilities. The motions of a disabled body (paraplegic/quadriplegic) may be captured. And a database of exercises specifically developed for that population may be created. The present invention includes independent exercise through characters resembling both able bodied patients and disabled bodied patients. The present invention may also reduce health/medical services provider visits for patients whose condition requires multiple caregiver appointments, thereby saving money and increasing patient self-reliance, autonomy, and self-confidence, while still providing the protection of a 'watchful eye'.

One embodiment of the present invention may include a panic button to facilitate notification of a care giver, authorities or 911, if necessary.

In another embodiment, an end user can access the site through specialized disability devices that interface with the system. A patient may choose from a variety of languages/learning styles (closed captions, disability options, Braille, sign language, auditory-read aloud etc.)

Another embodiment may offer continuity of care to a Health/Medical Services Organization and their staff or a third party (such as a family member) by creating a central repository for treatment plans, feedback, and caregiver collaboration. These features reduce malpractice, mistakes, gaps in care and misunderstandings due to illegible notes and allow multiple caregivers to deliver precise care. These features also ensure that residents will always receive the highest standard of care possible regardless of ability to communicate with caregiver on duty.

The present invention improves the social issue of disability by meeting the needs of the populations that are involved in the Provider/End user/Payer triad. The present invention motivates learning, reduces fraud and mis-spent revenue/time, and standardizes the therapeutic variables so that the therapy is safer and more effective and productive.

One embodiment of the present invention includes an advertising model that enhances the therapy experience, resulting in greater patient recall and enjoyment and the generation of revenue that can be used to enhance patient care and education. Through the appropriate use of sponsors, behaviors can be rewarded and a positive profit model can be created for physical therapists, who may generate revenue from additional services that they provide rather than from billing codes alone. Patients can learn about additional health initiatives offered by the physical therapist or affiliated, allied Health/Medical Services Organizations (appropriate for their condition) and can opt to learn more or get a referral to another health specialist.

In one embodiment, appropriate advertisers can sponsor step by step tutorials that can be paid for by sales of the advertised product. In one embodiment, a health/medical services provider can provide the specific education appropriate for patient care. A patient can learn in a step by step, self-paced model that can be provided regardless of the cost incurred to film and maintain each educational movie/clip. In this innovative approach, the present invention caters to the needs of the patient, allowing a Health/Medical Services Organization to meet its care obligations to the patient but also to make the transaction cost effective, and profitable, by allowing the sponsors to promote their products while offering information and step by step tutorials.

In one embodiment, patients are awarded with prizes at each level of accomplishment for reaching therapeutic milestones. In another embodiment, prizes are provided by advertisers. In another embodiment, the site is a vehicle for alerting patient to continued education by participation with a Health/Medical Services Organization's recommended products, classes, and services.

Another embodiment increases the "fun factor" by allowing a patient to dress the character in the latest fashions, listen to the latest music or purchase their own home versions of the products and services that are seen in the therapeutic environment.

In another embodiment, hospitals that are affiliated with the individual providers can alert patients to services that they provide, thereby allowing hospitals greater recognition, and increasing the likelihood of patient loyalty.

In another embodiment, a health/medical services provider puts the treatment plan into the system and lets the system know when to amend it criteria selected by the provider that corresponds with patient behavior and healing. In another embodiment, the system can alert the Health/Medical Services Organization if a patient has fallen behind or if the treatment plan is too aggressive.

In another embodiment, a health/medical services provider can make efficient/simple adjustments to the patient prescription via a mobile device or other electronic device. In another embodiment, a time saver "quick pick" is built into the system. This features also protects the patient. When a "quick pick" option is selected, a patient treatment plan based upon statistical data and patient provided profile criteria is generated. If a provider chooses the Quick Pick option, the system will check that the patient's educational boundaries are met so that mistakes or oversights are not made in patient care. One embodiment of the present invention includes an "open source" compilation of a database to allow the health/medical services provider to specify what it needs to best serve the unique needs of the population in its care.

The present invention offers many benefits to a payer (i.e., Medicare, Medicaid, etc.) including:

Third party payers have control over the variables in the physical therapy process that cause incomplete care and waste money due to skewed results. By ensuring the patient has been provided the proper information, has learned that information and has participated to the highest degree possible, quality and efficiency are increased, and the chance of injury is decreased.

Fraud is reduced because the present invention standardizes details of the therapeutic interaction. In addition, care givers who are unnecessarily billing excessive codes are exposed. That benefits insurance companies and is invisible to the therapist/doctor provider.

Since patient participation is encouraged and standardized, the present invention can expose patients who intend to stay on disability/workers compensation by non-compliance with a health/medical services provider's instructions. It can also help patients, who are on long term disability yet do not wish to remain injured, to get the necessary education and instructions to achieve a full and lasting recovery and to help them work towards physical competence The present invention reduces malpractice lawsuits from patient to care giver, lawsuits filed by Payers to providers who they suspect of fraud etc. When accusations of harm are made, data collected from the present invention (as well as the ability to teach the patient the required information) ensures that the therapeutic transaction is thorough and cost-effective.

The present invention allows accurate disability research data to be generated via real time performance, rather than assumptions or conjecture. It also allows insurance companies to make decisions based on the facts.

The present invention is ideal for research trials because it is able to control variables The present invention is also suitable for government driven social initiatives like smoking cessation and obesity management as it motivates end users and bridges the gap that has previously prevented people from participating in social initiatives.

The present invention allows patients who have low cost medical care/no medical care to receive a higher standard of care, as well as the education they need to meet their unique needs. Due to budget constraints, these people are currently forced to seek therapy from providers who sometimes must prioritize quantity over quality, seeing more patients and billing more codes in order to remain solvent. Paradoxically, this population is more likely to have language barriers, learning disabilities, obesity and other factors that necessitate better therapy which is not cost effective or possible. With the present invention, patients, regardless of personal characteristics or financial status, receive the care that they need for a full recovery.

While the above invention has been described with reference to certain preferred embodiments, the scope of the present invention is not limited to these embodiments. One skilled in the art may find variations of these preferred embodiments which, nevertheless, fall within the spirit of the present invention, whose scope is defined by the claims set forth below.

What is claimed is:

1. A system for providing a medical treatment program comprising:
    a first module executing on one or more servers for receiving data about a patient and for receiving an identification of one or more exercises selected for inclusion in the program;
    a second module executing on said one or more servers for displaying at least one of said exercises in said program to the patient and for collecting feedback information on said at least one exercise from the patient, said feedback information comprising one or more of the following: a perceived level of difficulty by the patient, a perceived level of pain by the patient, or a time that feedback on said exercise was entered;
    a database for storing said program and said feedback information; and
    a third module for comparing exercise information on said at least one exercise to said feedback information to determine the likelihood that the patient performed said at least one exercise correctly, said exercise information on said at least one exercise comprising one or more of the following: a time that said exercise was displayed, an anticipated level of difficulty for said exercise, an anticipated level of pain for said exercise, or an anticipated amount of time required to perform said exercise properly; and said third module determining the likelihood that the patient performed the at least one exercise correctly based on one or more of the following: comparing the anticipated level of difficulty for said exercise with the perceived level of difficulty, comparing the anticipated level of pain for said exercise with the perceived level of pain, or comparing the anticipated amount of time required to perform said exercise properly with a difference between the time said exercise was displayed and the time that the feedback on said exercise was entered.

2. A method for providing a medical treatment program comprising the steps of:

receiving by a first module executing on one or more servers data about a patient and an identification of one or more exercises selected for inclusion in the program;

sending by a second module executing on said one or more servers information regarding at least one of said exercises in said program for display to the patient and collecting feedback information on said at least one exercise from the patient, said feedback information comprising one or more of the following: a perceived level of difficulty by the patient, a perceived level of pain by the patient, or a time that feedback on said exercise was entered;

storing said program and said feedback information in a database; and comparing by a third module exercise information on said at least one exercise to said feedback information to determine the likelihood that the patient performed said at least one exercise correctly, said exercise information on said at least one exercise comprising one or more of the following: a time that said exercise was displayed, an anticipated level of difficulty for said exercise, an anticipated level of pain for said exercise, or an anticipated amount of time required to perform said exercise properly; and said third module determining the likelihood that the patient performed the at least one exercise correctly based on one or more of the following: comparing the anticipated level of difficulty for said exercise with the perceived level of difficulty, comparing the anticipated level of pain for said exercise with the perceived level of pain, or comparing the anticipated amount of time required to perform said exercise properly with a difference between the time said exercise was displayed and the time that the feedback on said exercise was entered.

3. Computer executable software code stored on a computer readable medium, the code for providing a medical treatment program, the code comprising:

code to receive by a first module executing on one or more servers data about a patient and an identification of one or more exercises selected for inclusion in the program;

code to send by a second module executing on said one or more servers information regarding at least one of said exercises in said program for display to the patient and collecting feedback information on said at least one exercise from the patient, said feedback information comprising one or more of the following: a perceived level of difficulty by the patient, a perceived level of pain by the patient, or a time that feedback on said exercise was entered;

code to store said program and said feedback information in a database; and code to compare by a third module exercise information on said at least one exercise to said feedback information to determine the likelihood that the patient performed said at least one exercise correctly, said exercise information on said at least one exercise comprising one or more of the following: a time that said exercise was displayed, an anticipated level of difficulty for said exercise, an anticipated level of pain for said exercise, or an anticipated amount of time required to perform said exercise properly; and said third module determining the likelihood that the patient performed the at least one exercise correctly based on one or more of the following: comparing the anticipated level of difficulty for said exercise with the perceived level of difficulty, comparing the anticipated level of pain for said exercise with the perceived level of pain, or comparing the anticipated amount of time required to perform said exercise properly with a difference between the time said exercise was displayed and the time that the feedback on said exercise was entered.

* * * * *